United States Patent [19]

Couch, Jr.

[11] 4,263,905

[45] Apr. 28, 1981

[54] DECUBITOUS BOOT

[76] Inventor: Thomas E. Couch, Jr., 17 White Fir Dr., Loudonville, N.Y. 12211

[21] Appl. No.: 896,006

[22] Filed: Apr. 13, 1978

[51] Int. Cl.³ ............................................. A61B 19/00
[52] U.S. Cl. ........................... 128/149; 128/DIG. 20; 128/153
[58] Field of Search ..................... 128/153, 80 R, 149, 128/DIG. 20, 81 R, 80 H, 166; 36/88, 93, 83, 71, 84, 95

[56] References Cited

U.S. PATENT DOCUMENTS

| | | | |
|---|---|---|---|
| 384,274 | 6/1888 | Pelton | 128/399 |
| 830,661 | 9/1906 | Gresham | 2/24 |
| 2,069,034 | 1/1937 | Hicks | 128/81 R |
| 2,880,721 | 4/1959 | Corcoran | 128/DIG. 20 |
| 2,911,657 | 11/1959 | Streeter | 128/149 |
| 3,020,910 | 2/1962 | Ward | 128/132 |
| 3,256,879 | 6/1966 | Hipps | 128/149 |
| 3,308,491 | 3/1967 | Spence | 128/153 |
| 3,407,406 | 10/1968 | Werner et al. | 128/153 |
| 3,511,233 | 5/1970 | Holy, Jr. | 128/149 |
| 3,685,176 | 8/1972 | Rudy | 36/71 |
| 3,744,161 | 7/1973 | Herunter | 36/93 |
| 3,901,228 | 8/1975 | Brown | 128/133 |
| 4,076,022 | 2/1978 | Walker | 128/149 |
| 4,135,504 | 1/1979 | Spann | 128/80 A |

FOREIGN PATENT DOCUMENTS 840452  4/1939  France ............................ 128/DIG. 20

Primary Examiner—Robert W. Michell
Assistant Examiner—Thomas Wallen
Attorney, Agent, or Firm—Heslin & Watts

[57] ABSTRACT

A boot-like appliance is formed of a resilient or inflatable material intended to generally envelop a patient's foot and lower leg area. The device is provided with suitable apertures to eliminate pressure points at bony prominences. Valves are provided in the inflatable model in order to permit the circulation of gases, liquids, or semisolids.

25 Claims, 3 Drawing Figures

DECUBITOUS BOOT

BACKGROUND OF THE INVENTION

This invention relates to medical appliances which can be used to avoid decubitous and other pressure-related ulcerations in bedridden patients, most particularly in connection with the lower extremities.

As is well known, ulcerations commonly referred to as "bed sores" develop when a patient is bedridden for any considerable length of time. These ulcerations usually appear at the location of bony eminences due to the concentration of pressure caused at these points.

There are a number of existing devices which are intended to be used in the prevention or healing of such sores or ulcerations. For use in the area of the patient's feet there are such things as heel cups, bed rolls, slings, fleece or foam, water mattresses and splints. Examples of these devices are found in the following U.S. patents: H. E. Hipps, U.S. Pat. No. 3,256,879; Brown, U.S. Pat. No. 3,901,228 and W. R. Spence, U.S. Pat. No. 3,308,491, particularly FIG. 12. Each of these devices has certain problems and practical difficulties associated with its use resulting in a tendency on the part of hospital staff not to employ them prophylactically. Heel cups, which are nothing more than cup-shaped devices tied around the front of the ankle, slip off easily. Bedrolls, which consist of a rolled up sheet, are frequently kicked over as the patient rolls from one position to another in the bed. Water mattresses, although highly beneficial for the purpose under consideration, are extremely expensive. Slings are hard to apply and restrict the patient to lying on his back.

It may be seen that the general approach taken in prior art appliances is to provide continuous padding at the anticipated pressure points on the person's body. The approach taken in this invention is to provide a structure which will be open at these points and, thus relieve the pressure and transfer it to other areas.

SUMMARY OF THE INVENTION

It is therefore an object of this invention to provide a device for the prevention of decubitous ulcerations of the lower extremities which is relatively easy to apply to the foot and lower leg of a patient and which will not easily slip off.

It is a further object of this invention to provide a device of the type indicated which will eliminate pressures normally experienced at points of bony prominence on a patient's foot.

It is a further object of this invention to provide a device of the type indicated which will leave a bedridden patient free to assume any desired position without interfering with the effectiveness of the invention.

The invention consists of a resilient material suitably shaped to generally envelop the heel and foot area of the patient's leg and having annular openings into which bony prominences may protrude in order to relieve pressure at these points.

DESCRIPTION OF THE PREFERRED EMBODIMENT

Figure 1:
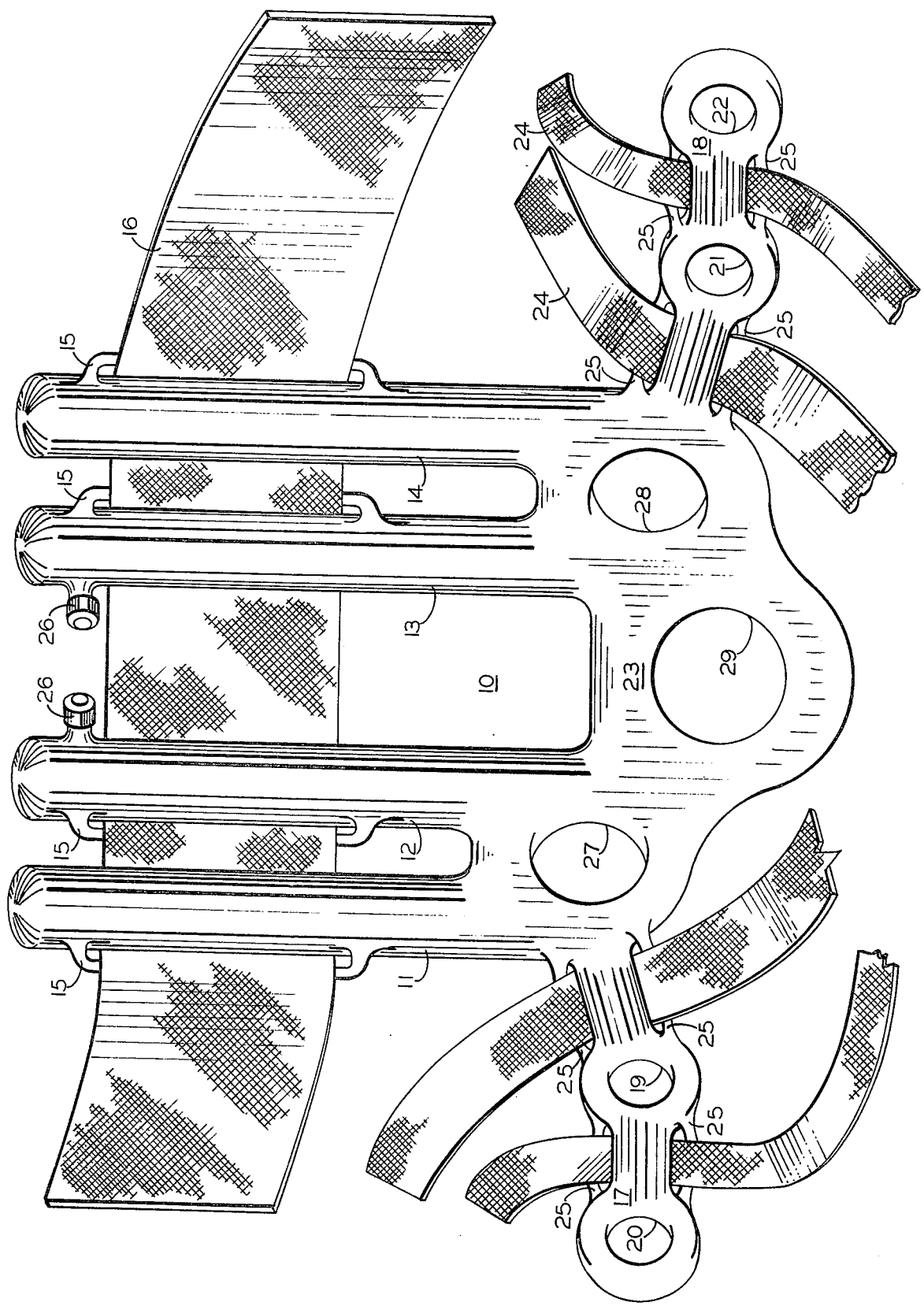
FIG. 1 is a front elevation of the invention with the medial and lateral extensions spread apart.

In FIG. 1, the invention, which may generally be referred to as a boot 10, is shown to have upright support members 11, 12, 13 and 14. The purpose of these supports is to assist in holding the appliance on the patient's foot. Each support member is provided with one or more loops 15 through which a strap 16 may be threaded. Strap 16 may be of the type which adheres to itself when pressed together, such as those sold under the trademark VELCRO so that it can be conveniently fastened around the patient's leg.

Medial and lateral extension members 17 and 18 respectively, are provided for protecting the medial and lateral portions of the patient's foot. Medial extension member 17 is provided with annular openings 19 and 20 so as to correspond with the location of the first metatarsal cuneiform articulation and the first metatarsal phalangeal articulation of the patient's foot. Similarly, annular openings 21 and 22 are provided to correspond respectively with the location of the base of the 5th metatarsal and the head of the 5th metatarsal of the patient's foot. The purpose of annular openings 19, 20, 21 and 22 is to avoid the creation of pressure of the boot itself against the bony prominences just described. At the same time, it will be appreciated that these same areas of bony prominence will be prevented by the structure of the boot surrounding them from pressing down on the bed as a patient lies there. In effect, the pressure which would normally be created at an area of bony prominence is transferred and spread by the structure of the invention to surrounding areas.

Loops 25 are provided in both the medial extension member 17 and the lateral extension member 18 for securing straps 24 which, again, may be made of VELCRO or any other suitable material.

The remaining portion of the boot generally covers the patient's heel. This heel member 23 is provided with annular openings 27 and 28 for the medial malleolus and lateral malleolus respectively. The location of opening 27 is preferably somewhat higher on the boot than opening 28 since the medial malleolus is somewhat higher on the patient's foot than the lateral malleolus. Annular opening 29 is provided to accommodate the tuberosity of the calcaneus. Again, the structure just described will serve to transfer pressure from the named areas of bony prominence and spread it over the surrounding areas of the patient's foot.

Figure 2:
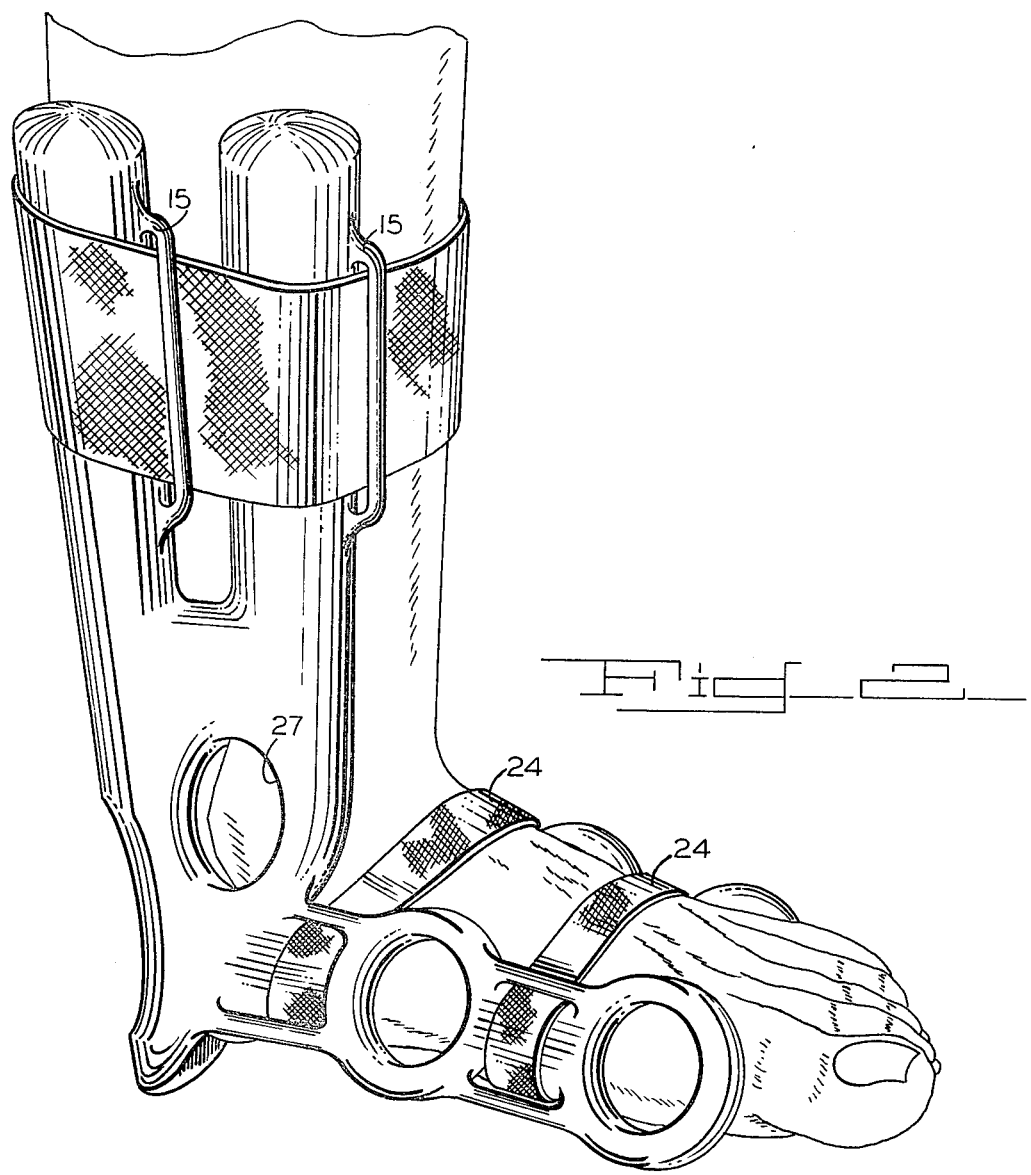
FIG. 2 is a perspective view from the medial aspect of a patient's foot showing the invention secured thereto in the intended manner.

The manner in which the boot is applied to the patient is readily understood by reference to FIG. 2.

It is recommended that the invention be made of a resilient material such as polyurethane or some similar material. The use of such material will result in relatively even distribution of pressure around the areas of bony prominence mentioned above. It is also advantageous to form the boot 10 in such a way that it will be inflatable. Valves 26 are provided for the purpose of inflating the boot with air or a liquid. By providing two such valves 26 of appropriate dimensions, the boot may be used in combination with a circulatory system to pass water or another liquid, possibly temperature controlled, through the boot for certain therapeutic purposes. For example, it is well known to be advantageous under some circumstances to apply heat to a patient's foot. An example of the kind of circulatory system with which the boot can be used is the Aqua-K-Pad system manufactured by Gorman-Rupp Company of Mansfield, Ohio. Valves 26 should be located so as not to cause pressure against the patient's leg.

The overall thickness of the structural members of the boot 10 should be sufficient to hold each area of bony prominence away from the bed. For normal patients, an average thickness of an inch or so is very adequate.

It should be noted that it is advantageous to form the device without biasing its shape for use on a right or a left foot. A device so formed would tend to lie flat when not in use. In this way, a single device could be used for either the right or left foot depending upon which way it was applied to the person's foot. This is so because the openings 19, 20, 21 and 22 are generally of the same size while the openings 27 and 28 are also of the same size. The exact dimensions of these various openings is not particularly critical. However, it is recommended that the openings in the medial and lateral extension members be approximately 1 inch in diameter while openings 27 and 28 in the heel member be about 1.5 inches in diameter. Opening 29 should be approximately 2 inches in diameter. The edges of the opening, which will be in contact with the patient's foot, should preferably be smooth and devoid of sharp edges or seams.

Figure 3:
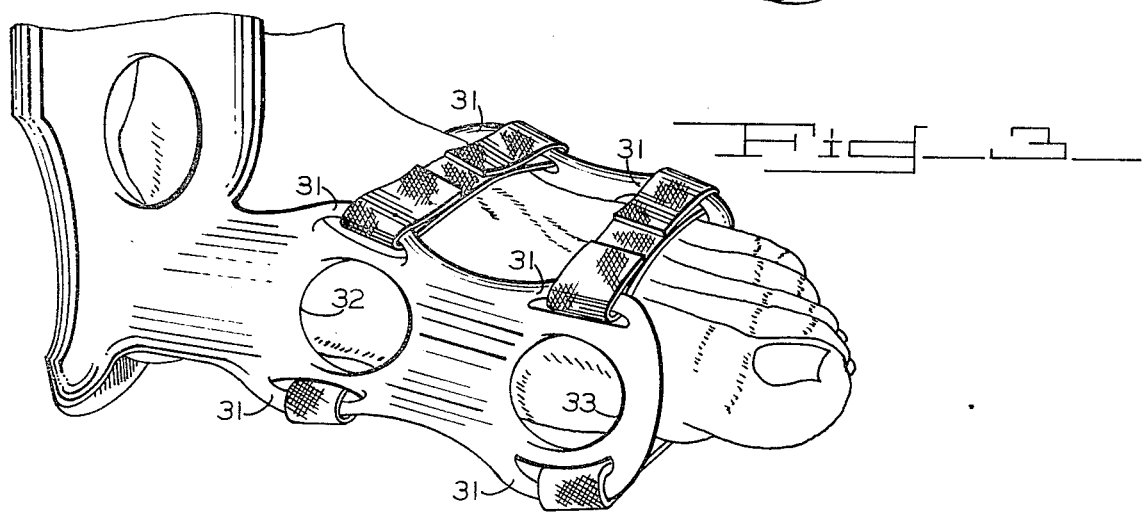
FIG. 3 is a view of a portion of the invention from the same perspective showing an alternate embodiment of the invention.

FIG. 3 shows an alternate embodiment of the invention in which loops 31 are provided at the approximate location of annular openings 32 and 33 on the medial extension member of the boot. Although not visible in FIG. 3, the lateral extension member is provided with similar loops and annular openings. The location, size and function of all the annular openings are the same for this embodiment as in the embodiment of FIG. 2. The advantage of this particular embodiment is that it tends to provide more tension between the medial extension member and the lateral extension member at the points where the bony eminences are located, thereby rendering the device more securely attached to the patient's foot. This is particularly helpful in the case of a patient who moves in bed quite frequently and who would have a greater tendency to kick off the boot.

Clearly, various modifications could be made to this invention without departing from the spirit thereof. It is intended to encompass all such modifications within the following claims.

I claim:

1. A decubitous boot for bedridden patients comprising:
   a heel member adapted to envelop the patient's heel area and having annular apertures therein adapted to engage the tuberosity of the calcaneus, the medial malleolus and lateral malleolus;
   a plurality of support members attached to the heel member and adapted to extend upwardly from the patient's ankle and along his lower leg;
   a medial extension member attached to the heel member and adapted to run along the medial aspect of the foot and having annular apertures therein adapted to engage the first metatarsal cuneiform articulation and the first metatarsal phalangeal articulation; and
   a lateral extension member attached to the heel member and adapted to run along the lateral aspect of the foot and having annular apertures therein adapted to engage the base of the 5th metatarsal and the head of the 5th metatarsal.

2. The invention of claim 1 wherein the boot is made of a resilient material.

3. The invention of claim 2 wherein means are provided for securing the boot to the patient's foot with each of the annular apertures aligned over its associated area of bony prominence on the foot.

4. The invention of claim 1 wherein the boot is made of a flexible material formed with a hollow interior so as to be inflatable, and wherein at least one valve is provided in communication with the interior of the boot for inflation of same.

5. The invention of claim 4 wherein the boot is provided with at least one inlet valve and one outlet valve, each communicating with the interior of the boot, whereby a fluid may be circulated through the boot.

6. The invention of claim 5 wherein means are provided for securing the boot to the patient's foot with each of the annular apertures aligned over its associated area of bony prominence on the foot.

7. A decubitous boot for bedridden patients comprising:
   a heel member adapted to envelop the patient's heel area and having annular apertures therein adapted to engage the tuberosity of the calcaneus, the medial malleolus and lateral malleolus;
   a medial extension member attached to the heel member and adapted to run along the medial aspect of the foot and having annular apertures therein adapted to engage the first metatarsal cuneiform articulation and the first metatarsal phalangeal articulation; and
   a lateral extension member attached to the heel member and adapted to run along the lateral aspect of the foot and having annular apertures therein adapted to engage the base of the fifth metatarsal and the head of the fifth metatarsal.

8. The invention of claim 7 wherein the boot is made of a resilient material.

9. The invention of claim 10 wherein means are provided for securing the boot to the patient's foot with each of the annular openings aligned over its associated area of boney prominence on the foot.

10. The invention of claim 7 wherein the boot is made of a flexible material formed with a hollow interior so as to be inflatable, and wherein at least one valve is provided in communication with the interior of the boot for inflation of same.

11. The invention of claim 10 wherein the boot is provided with at least one inlet valve and one outlet valve, each communicating with the interior of the boot, whereby a fluid may be circulated through the boot.

12. The invention of claim 11 wherein means are provided for securing the boot to the patient's foot with each of the annular openings aligned over its associated area of boney prominence on the foot.

13. A decubitous boot for bedridden patients comprising:
   a heel member adapted to envelop the patient's heel area and having at least one aperture therein, each such aperture adapted to permit at least one boney prominence of the heel to protrude therethrough;
   a medial extension member attached to the heel member and adapted to run along the medial aspect of the foot and having at least one aperture therein, each such aperture adapted to permit at least one boney prominence located along the medial aspect of the foot to protrude therethrough; and a lateral extension member attached to the heel member and adapted to run along the lateral aspect of the foot and having at least one aperture therein, each such aperture adapted to permit at least one boney prominence located along the lateral aspect of the foot to protrude therethrough.

14. The invention of claim 13 wherein the boot is made of a resilient material.

15. The invention of claim 14 wherein means are provided for securing the boot to the patient's foot with each of the apertures aligned over its associated area or areas of boney prominence on the foot.

16. The invention of claim 13 wherein the boot is made of a flexible material formed with a hollow interior so as to be inflatable, and wherein at least one valve is provided in communication with the interior of the boot for inflation of same.

17. The invention of claim 16 wherein the boot is provided with at least one inlet valve and one outlet valve, each communicating with the interior of the boot, whereby a fluid may be circulated through the boot.

18. The invention of claim 17 wherein means are provided for securing the boot to the patient's foot with each of the apertures aligned over its associated areas or areas of boney prominence on the foot.

19. A decubitous boot for bedridden patients comprising:

an elongated relatively narrow body having a central aperture adapted to engage the tuberosity of the calcaneus, said body including a medial extension member having annular apertures therein adpated to engage the medial malleolus, the first metatarsal cuneiform articulation and the first metatarsal phalangeal articulation, said body further including a lateral extension member having annular apertures therein adapted to engage the lateral malleolus, the base of the fifth metatarsal and the head of the fifth metatarsal and a means for securing the boot to the patient's foot.

20. A decubitous boot for bedridden patients comprising:

an elongated relatively narrow body having a central aperture adapted to engage the patient's heel, said body including a medial extension member having at least one aperture therein, each such aperture being adapted to engage at least one boney prominence located on the medial aspect of the wearer's foot said body further including a lateral extension member having at least one aperture therein, each such aperture being adapted to engage at least one boney prominence located on the lateral aspect of the wearer's foot and a means for securing the boot to the patient's foot.

21. The invention of claim 19 or 20 wherein the boot is made of a resilient material.

22. The invention of claim 21 wherein the boot has a hollow interior so as to be inflatible, and wherein at least one valve is provided in communication with the interior of the boot for inflation of the same.

23. The invention of claim 22 wherein the boot is provided with at least one inlet valve and one outlet valve, each communicating with the interior of the boot, whereby a material may be circulated through the boot.

24. The invention of claim 21 wherein the securing means comprises a plurality of support members attached to the boot and adapted to extend upwardly from the patient's ankle and along his lower leg.

25. The invention of claim 20 wherein the apertures located along the medial extension member are adapted to engage the medial malleolus, the first metatarsal cuneiform articulation and the first metatarsal phalangeal articulation; and the apertures located along the lateral extension member are adapted to engage the lateral malleolus, the base of the fifth metatarsal, and the head of the fifth metatarsal.

* * * * *